United States Patent [19]

Petitou et al.

[11] Patent Number: 5,382,570
[45] Date of Patent: Jan. 17, 1995

[54] SULFATED GLYCOSAMINOGLYCANOID DERIVATIVES OF THE DERMATAN SULFATE AND CHONDROITIN SULFATE TYPE

[75] Inventors: Maurice Petitou, Paris, France; Constant A. A. van Boeckel, Lx Oss, Netherlands

[73] Assignees: Akzo, N.V., Velperweg; Snofi, S.A., Arnhem, Netherlands

[21] Appl. No.: 919,683

[22] Filed: Jul. 27, 1992

Related U.S. Application Data

[63] Continuation-in-part of Ser. No. 795,595, Nov. 21, 1991, abandoned, which is a continuation-in-part of Ser. No. 690,035, Apr. 23, 1991, abandoned.

[30] Foreign Application Priority Data

Apr. 23, 1990 [EP] European Pat. Off. ........... 90201006

[51] Int. Cl.⁶ .................. A61K 31/70; A61K 31/715; C07H 13/12; C07H 23/00
[52] U.S. Cl. .......................... 514/53; 514/54; 514/61; 536/118; 536/120; 536/121
[58] Field of Search .................. 536/118, 120, 121; 514/53, 54, 61

[56] References Cited

U.S. PATENT DOCUMENTS

| | | | |
|---|---|---|---|
| 3,301,848 | 1/1967 | Halleck | 536/118 |
| 4,105,760 | 8/1978 | Szejtli et al. | 536/118 |
| 4,221,907 | 9/1980 | Nair et al. | 536/118 |
| 4,818,816 | 4/1989 | Petitou et al. | 536/118 |
| 4,841,041 | 6/1989 | van Boeckel et al. | 536/118 |

OTHER PUBLICATIONS

Cancer Research, vol. 49, issued Aug. 1, 1989, Tietze et al, "Proton–Mediated Liberation of Aldophamide from a Nontoxic Prodrug: A Strategy for Tumor–Selective Activation of Cytocidal Drugs", pp. 4179–4184.

Primary Examiner—John W. Rollins
Assistant Examiner—Everett White
Attorney, Agent, or Firm—William M. Blackstone; Mary E. Gormley

[57] ABSTRACT

The invention relates to sulfated glycosaminoglycanoid derivatives of the dermatan sulfate and chondroitin sulfate type, of which N-sulfate, N-acetate, and hydroxy groups, are replaced by alkoxy, aryloxy, aralkoxy, or O-sulfate groups. The compounds have antithrombotic and smooth muscle cell proliferation inhibiting activities.

5 Claims, No Drawings

SULFATED GLYCOSAMINOGLYCANOID DERIVATIVES OF THE DERMATAN SULFATE AND CHONDROITIN SULFATE TYPE

This is a continuation-in part of application Ser. No. 07/795,595, filed Nov. 21, 1991, now abandoned, which is a continuation-in-part of U.S. Ser. No. 07/690,035 filed Apr. 23, 1991, now abandoned.

The invention concerns sulfated glycosaminoglycanoid derivative of the dermatan sulfate and chondroitin sulfate type, of which N-sulfate, N-acetate, and hydroxy groups, are replaced by alkoxy, aryloxy, aralkoxy, or O-sulfate groups. The invention is further related to a process for the preparation of said derivative, a pharmaceutical composition containing the same, and a method of treatment using said derivatives.

Sulfated glycosaminoglycan derivatives are known. European patent EP 84,999, for instance, discloses sulfated pentasaccharides of the chemical class of glycosaminoglycans having antithrombotic activity. These known compounds can possess, apart from hydroxy groups, O-sulfate, N-sulfate, and N-acetyl groups, whereas the anomeric hydroxy group is sometimes replaced by a methoxy group.

In contrast to the known compounds, the present sulfated glycosaminoglycanoid derivatives do not have free hydroxy groups, nor do they possess N-sulfate or N-acetate groups.

It has now been found that the compounds of this invention have a better binding affinity to heparin cofactor II (HCII), which results in a better pharmacokinetic profile, longer half-life times, and lower therapeutic doses and thus lesser side-effects. Furthermore, the compounds of this invention have a substantially better heparin cofactor II mediated antithrombin activity, and are, therefore, more effective as thrombin generation inhibitors than the prior art compounds. The sulfated glycosaminoglycanoid derivatives can also be used as inhibitors for smooth muscle cell proliferation, and for the treatment of angiogenesis.

The inclusion of alkyl, aryl, or agalkyl functionalized saccharide units gives further a very important synthetic advantage over the prior art compounds. By functionalizing the hydroxy groups with alkyl, aryl, or aralkyl groups, it is in most cases redundant to prepare temporarily protected carbohydrates, which makes the synthetic pathway considerably shorter and simpler, whereas the replacement of the glucosamine units by glucose units further simplifies the synthesis of the saccharides significantly. Moreover, an additional advantage of the synthesis of the compounds of the invention is that the nature of the temporarily protective groups, which are necessary for the protection of the hydroxy groups to be sulfated, is not critical.

More specifically, the compounds according to this invention are sulfated glycosaminoglycanoid derivatives, comprising the disaccharide unit having the formula I or II

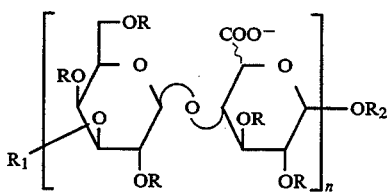

I

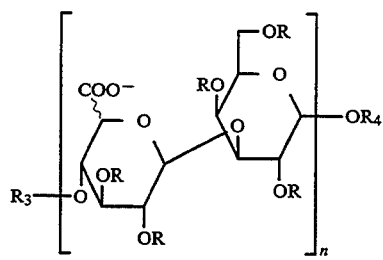

II in which the twitched lines denote an α or β bond, n is the number 1–4, and preferably 1 or 2, each of the groups R are independently selected from the group consisting of alkyl and sulfate; $R_1$ has the same meaning as R or is

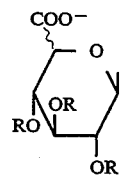

wherein the twitched line and R have the previously given meanings; $R_2$ is alkyl, aryl, aralkyl or β-

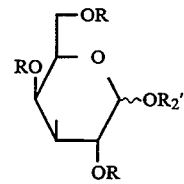

wherein the twitched line and R have the previously given meanings and $R_2'$ is alkyl, aryl or aralkyl; $R_3$ has the same meaning as R or is

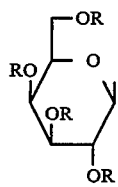

wherein R has the previously given meaning, and $R_4$ is alkyl, aryl, aralkyl, or β-

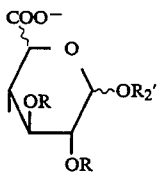

wherein the twitched lines, R, and $R_2''$ have the previously given meanings; and the charged moieties are compensated by counter-ions.

Preferred compounds have the disaccharide unit of the general formula III or IV

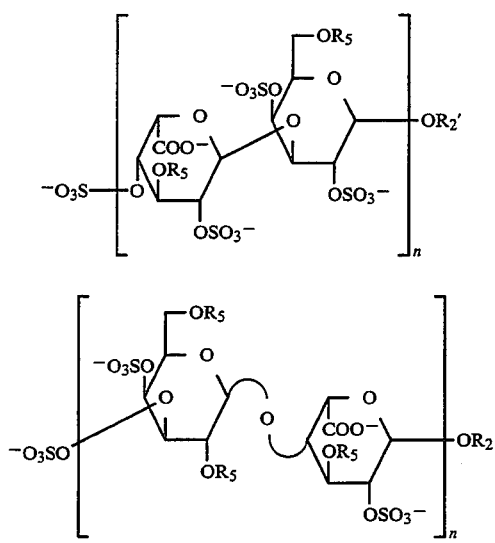

wherein n, $R_2$, and $R_2'$ have the previously given meanings and $R_5$ is methyl or ethyl; and the charged moieties are compensated by counter-ions.

The alkyl group in the definition of R, $R_1$, $R_2$, $R_2'$, $R_3$ and $R_4$ is a branched or unbranched alkyl group having 1-8 carbon atoms or a cyclo-alkyl group having 3-8 carbon atoms. Alkyl groups for different groups R, $R_1$, $R_2$, $R_2'$, $R_3$, or $R_4$ may be different. Examples are methyl, ethyl, isopropyl, butyl, sec-butyl, pentyl, neopentyl, hexyl, and octyl. Preferred are the alkyl groups having 1-6 carbon atoms. More preferred are the alkyl groups having 1-4 carbon atoms, and most preferred are the methyl and ethyl groups.

The term aryl in the definition of $R_2$, $R_2'$, and $R_4$ means an aromatic group, preferably phenyl, which may be substituted by OH, alkyl having 1-4 carbon atoms, alkoxy having 1-4 carbon atoms, halogen (preferably fluorine, chlorine, or bromine), $CF_3$, or $NR'R''$, wherein R' and R'' are independently hydrogen or alkyl having 1-4 carbon atoms, or R' is $SO_3^-$ and R'' is hydrogen.

The term aralkyl means an aralkyl group in which the alkyl moiety is an alkyl group having 1-4 carbon atoms and the aryl moiety is an aryl group as previously defined.

The term "α or β" means that the configuration of the concerned bond is respectively trans or cis with respect to the anomeric bond in the concerned saccharide unit, or when it concerns the anomeric bond itself, it has the usual meaning of carbohydrate chemistry.

The term sulfated glycosaminoglycanoid derivative means a sulfated glycosaminoglycan derivative, in which the N-sulfate group(s) is (are) replaced by alkoxy, and preferably by O-sulfate groups. A glycosaminoglycan is a carbohydrate which belongs to the well-known chemical class of glycosaminoglycans.

Preferred compounds have R alkyl, and more preferably methyl or ethyl, at sites where the corresponding naturally occurring glycosaminoglycans possess a free hydroxy group or an acetamido group.

It is generally believed that multipoint key polar interactions are of essential importance throughout molecular biology for ensuring high selectivity in non-covalent molecular associations, and that substitution of only one of the key hydroxy groups of an oligosaccharide by a hydrophobic group (and invariably a number of the hydroxy groups prove outstandingly essential to complex formation) can result in complete loss of the affinity by the protein. Remarkably, however, the preferred compounds of this invention having O-alkyl and O-sulfate groups without having free hydroxy groups, still show the full-blown activity.

The counter-ions which compensate the charged moieties are pharmaceutically acceptable counter-ions, like hydrogen, or more preferably alkali or earth-alkali metal ions, like sodium, calcium, or magnesium.

The carbohydrates according to this invention may be prepared according to well known methods described and used for the synthesis of polysaccharides. In this respect, particular reference is made to the previously mentioned European patent EP 84,999, in which methods for the synthesis of polysaccharides are disclosed.

A suitable process for the preparation of the sulfated glycosaminoglycanoid derivative of this invention is characterized in that protected monosaccharides are coupled to give protected disaccharides, which are optionally further coupled to tri- to hexasaccharides, after which the protective groups are partially or completely cleaved and free hydroxy groups are sulfated, after which, if present, remaining protective groups are cleaved, and the compound obtained is optionally converted into a pharmaceutically acceptable salt.

A stepwise condensation of the monosaccharides is possible. In general, however, building blocks consisting of D-galactose, D-glucuronic acid, or L-iduronic acid, suitably functionalized with the required alkyl, aryl, or aralkyl groups or by temporarily protective groups, are condensed together in the desired order. In this way the (protected) saccharide unit can be prepared, which can be coupled with other saccharide units, or protected derivatives thereof. Suitable protective groups are well known in carbohydrate chemistry. Preferred protective groups include benzyl and acetyl for hydroxy groups, and methyl and benzyl for the carboxylate group of uronic acids. Other protective groups like levulinoyl, chloroacetyl, trityl, benzoyl, and the like, may be used with equal success. Coupling of the saccharides is performed in a manner known in the art, e.g. deprotection of the 1-position of the glycosyl-donor, and/or activation of this position (e.g. by making a bromide, pentenyl, fluoride, thioglycoside, or trichloroacetamide derivative) and coupling the activated glycosyl-donor with an optionally protected glycosyl-acceptor.

This process of stepwise or building block synthesis affords for example a protected carbohydrate derivative comprising a tetrasaccharide unit of the general formulae I or II, but having protective groups at the positions where sulfate groups are attached. The protective groups are hydroxy protective group (preferably benzyl or acetyl). The protected carbohydrate derivative can be deprotected and sulfated in a manner as described in the previously mentioned EP 84,999 in order to obtain the carbohydrate derivative according to formulae I and II. Suitable deprotection methods are, for example, basic hydrolysis for acetyl-and methyl-esters, and hydrogenolysis for benzyl ethers. Sulfation can successfully be performed with complexes of sulfur trioxide with bases like trimethylamine, triethylamine or pyridine in a suitable solvent.

For the treatment of venous thrombosis or for the inhibition of smooth muscle cell proliferation the compounds of the invention may be administered enterally or parenterally, and for humans preferably in a daily dosage of 0.001–10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1 propyl O-2,6-di-O-ethyl-3,4-di-O-sulfo-β-D-galactopyranosyl-(1→4)-O-3-O-ethyl-2-O-sulfo-α-L-idopyranuronosyl-(1→3)-O-2,6-di-O-ethyl-4-O-sulfo-β-D-galactopyranosyl-(1→4)-O-3-O-ethyl-2-O-sulfo-α-L-idopyranuronoside heptakis sodium salt.

propyl O-4-O-benzoyl-2,6-di-O-ethyl-β-D-galactopyranosyl-(→4)-O-(methyl 2-O-benzoyl-3-O-ethyl-α-L-idopyranuronosyluronate)-(1→3)-O-4-benzoyl-2,6-di-O-ethyl-β-D-galactopyranosyl-(1→4)-O-(methyl-2-O-benzoyl-3-O-ethyl-α-L-idopyranuronoside uronate) (0.028 mmol) was dissolved in 2.79 ml of tetrahydrofuran. The mixture was cooled to −5° C. and 1.37 ml of a 33% hydrogen peroxide solution were added. After 10 min stirring 0.633 ml of a 1.25M lithium hydroxide hydrate solution in water were added. After 1 h stirring the temperature was increased to 0° C. and the mixture was stirred for another 20 h. The mixture was brought to room temperature and 2.56 ml of methanol and 0.65 ml of 4N sodium hydroxide were added. The mixture was stirred for another 20 h and acidified with diluted hydrochloric acid at 0°–5° C. The excess of hydrogen peroxide was destroyed with a 10% sodium sulfite solution in water and the mixture was evaporated to dryness. The residue was treated with 10 ml of dichloromethane-methanol (8:2), the salts were filtered, and the filtrate evaporated to dryness. The residue was purified on a Sephadex LH20 column and the pure fractions were pooled and evaporated to dryness to obtain propyl O-2,6-di-O-ethyl-β-D-galactopyranosyl-(1→4)-O-3-O-ethyl-α-L-idopyranuronosyl-(1→3)-O-2, 6-di-O-ethyl-β-D-galactopyranosyl-(1→4)-O-3-O-ethyl-α-L-idopyranuronoside, which was dissolved in a mixture of 1.63 ml of dry dimethylformamide and 0.64 mmol triethylamine sulfurtrioxide complex. The mixture was stirred for 20 h at 50 ° C., after which the mixture was cooled to room temperature and a mixture of 215 mg of sodium hydrogen carbonate in 2.8 ml of water were added. The mixture was stirred for 30 min and then evaporated to dryness. The residue was dissolved in water, desalted on Sephadex G-25, and the combined fractions were liophilized to give amorphous propyl O-2,6-di-O-ethyl-3,4-di-O-sulfo-β-D-galactopyranosyl-(1→4)-O-3-O-ethyl-2-O-sulfo-α-L -idopyranuronosyl-(1→3)-O-2,6-di-O-ethyl-4-O-sulfo-β-D-galactopyranosyl-(1→4)-O-3-O-ethyl-2-O -sulfo-α-L-idopyranuronoside heptakis sodium salt. $[\alpha]_D^{20} = -16.0°$ (c=1; water).

EXAMPLE 2

In a similar manner as described in Example 1 were prepared:

propyl O-2,6-di-O-ethyl-3,4-di-O-sulfo-β-D-galactopyranosyl-(1→4)-O-3-O-ethyl-2-O-sulfo-α-L -idopyranuronosyl-(1→3)-O-2,6-di-O-ethyl-4-O-sulfo-β-D-galactopyranosyl-(1→4)-O-3-O-ethyl-2-O -sulfo-α-L-idopyranuronosyl-(1→3)-O-2,6-di-O-ethyl-4-O-sulfo-β-D-galactopyranosyl-(1→4)-O-3-O-ethyl -2-O-sulfo-α-L-idopyranuronoside decakis sodium salt. $[\alpha]_D^{20} = -17.5°$ (c=1; water).

propyl O-2,6-di-O-ethyl-3,4-di-O-sulfo-β-D-galactopyranosyl-(1→4)-O-3-O-ethyl-2-O-sulfo-α-L -idopyranuronoside tetrakis sodium salt. $[\alpha]_D^{20} = -9.7°$ (c=1; water).

propyl O-2,6-di-O-ethyl-3,4-di-O-sulfo-β-D-galactopyranosyl-(1→4)-O-3-O-ethyl-2-O-sulfo-α-L -idopyranuronosyl-(1→3)-O-2,6-di-O-ethyl-4-O-sulfo-β-D-galactopyranosyl-(1→4)-O-3-O-ethyl-2-O -sulfo-α-L-idopyranuronosyl-(1→3)-O-2,6-di-O-ethyl-4-O-sulfo-β-D-galactopyranosyl-(1→4)-O-3-O-ethyl -2-O-sulfo-α-L-idopyranuronosyl-(1→3)-O-2,6-di-O-ethyl-4-O-sulfo-β-D-galactopyranosyl-(1→4)-O-3-O-ethyl-2-O-sulfo-α-L-idopyranuronosyl-(1→3)-O-2,6-di-O-ethyl-4-O-sulfo-β-D-galactopyranosyl-(1→4)-O -3-O-ethyl-2-O-sulfo-α-L-idopyranuronoside hexadecakis sodium salt.

4-methoxyphenyl O-3-O-methyl-2,4-di-O-sulfo-α-L-idopyranuronosyl-(1→3)-O-6-O-methyl-2,4-di-O-sulfo -β-D-galactopyranosyl-(1→4)-O-3-O-methyl-2-O-sulfo-α-L-idopyranuronosyl-(1→3)-O-6-O-methyl-2,4-di-O-sulfo-β-D-galactopyranosyl-(1→4)-O-3-O-methyl-2-O-sulfo-α-L-idopyranurosyl-(1→3)-O-6-O-methyl -2,4-di-O-sulfo-β-D-galactopyranoside tridecakis sodium salt. Anomeric protons chemical shift: 5.44; 5.42; 5.33; 5.21; 4.67; 4.65 ppm.

4-methoxyphenyl O-3-O-methyl-2,4-di-O-sulfo-α-L-idopyranuronosyl-(1→3)-O-6-O-methyl-2,4-di-O-sulfo -β-D-galactopyranoside pentakis sodium salt. Anomeric protons chemical shift: 5.29; 5.34 ppm.

4-methoxyphenyl O-3-O-methyl-2,4-di-O-sulfo-α-L-idopyranuronosyl-(1→3)-O-6-O-methyl-2,4-di-O-sulfo -β-D-galactopyranosyl-(1→4)-O-3-O-methyl-2-O-sulfo-α-L-idopyranuronosyl-(1→3)-O-6-O-methyl-2,4-di-O-sulfo-β-D-galactopyranoside nonakis sodium salt. Anomeric protons chemical shift: 5.44; 5.42; 5.22; 4.66 ppm.

We claim:

1. A sulfated compound derived from a glycosaminoglycan, comprising the disaccharide unit having the formula I or II

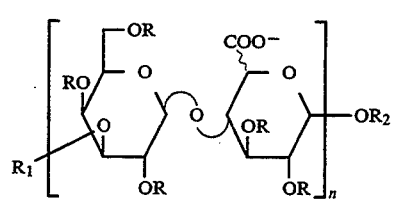

-continued

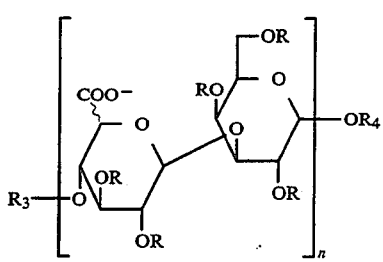

in which the twitched lines denote an α or β bond, n is the number 1 to 4, each of the groups R are independently selected from the group consisting of alkyl and sulfate; $R_1$ has the same meaning as R or is

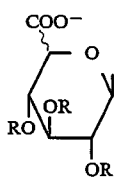

wherein the twitched line and R have the previously given meanings; $R_2$ is selected from the group consisting of alkyl, aryl, aralkyl and β-

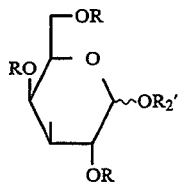

wherein the twitched line and R have the previously given meanings and $R_2'$ is selected from the group consisting of alkyl, aryl and aralkyl; $R_3$ has the same meaning as R or is

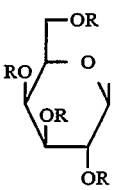

wherein R has the previously given meaning, and $R_4$ is selected from the group consisting of alkyl, aryl, aralkyl and β-

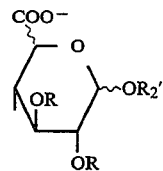

wherein the twitched lines, R, and $R_2'$ have the previously given meanings; and the charged moieties are compensated by counter-ions.

2. The compound according to claim 1 having the formula III

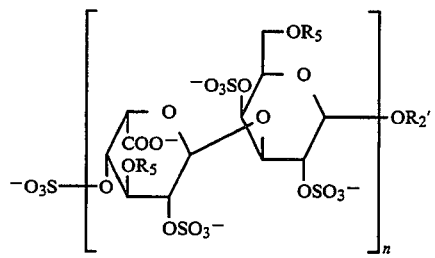

wherein n and $R_2'$ are as defined in claim 1; and $R_5$ is ethyl or methyl.

3. The compound according to claim 1 having the formula IV

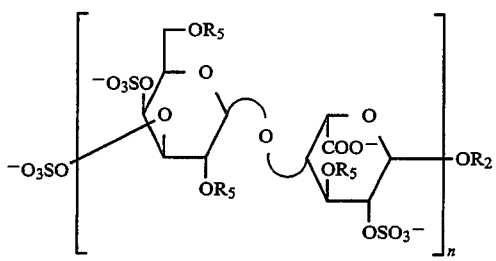

wherein n and $R_2$ are as defined in claim 1; and $R_5$ is ethyl or methyl.

4. A pharmaceutical composition comprising the sulfated compound according to claim 1 admixed with pharmaceutically acceptable auxiliaries.

5. A pharmaceutical composition comprising the sulfated compound according to claim 2 admixed with pharmaceutically acceptable auxiliaries.

* * * * *